(12) United States Patent
Elson et al.

(10) Patent No.: US 6,303,654 B1
(45) Date of Patent: Oct. 16, 2001

(54) ACYCLIC MONOTERPENOID DERIVATIVES

(75) Inventors: Charles E. Elson; Huanbiao Mo, both of Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/263,622

(22) Filed: Mar. 5, 1999

Related U.S. Application Data

(60) Provisional application No. 60/077,734, filed on Mar. 12, 1998.

(51) Int. Cl.$^7$ ............................. A01N 37/12; A01N 37/10

(52) U.S. Cl. ......................... 514/535; 514/532; 514/534; 514/546; 514/716; 514/717; 514/718; 514/722

(58) Field of Search ................................ 424/195.1, 725; 514/532, 534, 535, 546, 716, 717, 718, 722

(56) References Cited

U.S. PATENT DOCUMENTS

| | | |
|---|---|---|
| 5,466,718 | 11/1995 | Nakatsu et al. . |
| 5,567,729 | 10/1996 | Bradfute et al. . |

FOREIGN PATENT DOCUMENTS

| | | |
|---|---|---|
| WO 94/20080 | 9/1994 | (WO) . |
| WO 95/13059 | 5/1995 | (WO) . |

OTHER PUBLICATIONS

R.G. Bostedor, et al., "Farnesol–derived Dicarboxylic Acids in the Urine of Animals Treated with Zaragozic Acid A or with Farnesol," *J. Biol. Chem.*, 272:9197–9203 (Apr. 4, 1997).

Y.D. Burke, et al., "Inhibition of Pancreatic Cancer Growth by the Dietary Isoprenoids Farnesol and Geraniol," *Lipids*, 32:151–156.

C.C. Correll, et al., "Identification of Farnesol as the Non–sterol Derivative of Mevalonic Acid Required for the Accelerated Degradation of 3–Hydroxy–3–methylglutaryl–coenzyme A Reductase," *J. Biol. Chem.*, 269:17390–17393 (Jul. 1994).

C.E. Elson and S.G. Yu, "The Chemoprevention of Cancer by Mevalonate–Derived Constituents of Fruits and Vegetables," *Critical Review*, pp. 607–614 (1994), American Institute of Nutrition.

C.E. Elson, "Suppression of Mevalonate Pathway Activities by Dietary Isoprenoids: Protective Roles in Cancer and Cardiovascular Disease," Symposium: Nutritional Modulation of Lipid–Mediated Signal Transduction Systems, pp. 1666S–1672S (1995).

C.E. Elson and A.A. Qureshi, "Coupling the Cholesterol– and Tumor–suppressive Actions of Palm Oil to the Impact of Its Minor Constituents on 3–Hydroxy–3–Methylglutaryl Coenzyme A Reductase Activity," *Prostaglandins Leukotrienes and Essential Fatty Acids*, 52:205–208 (1995).

C.E. Elson, et al., "Functional Consequences of the modulation of 3–hydroxy–3methylglutaryl Coenzyme A$^1$ Reductase by Isoprenoids," *Am. Assoc. Canc. Res.,* Apr. 10, 1998 (Abstract).

C.E. Elson, et al., "Isoprenoid–Mediated Inhibition of Mevalonate Synthesis: Potential Application to Cancer," *Minireview*, pp. 294–311 (1999), Society for Experimental Biology and Medicine.

B.M. Forman, et al., "Identification of a Nuclear Receptor That Is Activated by Farnesol Metabolites," *Cell*, 81:687–693 (Jun. 2, 1995).

D. Gonzalez–Pacanowsky, et al., "Isopentenoid Synthesis in Isolate Embryonic Drosophila Cells," *Jl. Biol. Chem.*, 263:1301–1306 (Jan. 25, 1988).

L. He, et al., "Isoprenoids Suppress the Growth of Murine B16 Melanomas In Vitro and In Vivo," *Biochemical and Molecular Roles of Nutrients*, pp. 668–674 (1997) American Society for Nutritional Sciences.

G.J. Kelloff, R.A. Lubet, et al., "Farnesyl Protein Transferase Inhibitors as Potential Cancer Chemopreventives," *Cancer Epidemiology, Biomarkers and Prevention*, 6:267–282 (Apr. 1997).

R. Kothapalli, et al., "Farnesylamine: An Inhibitor of Farnesylation and Growth of Ras–Transformed Cells," *Lipids*, 28:969–973 (1993).

R.B. Lobell and N.E. Kohl, "Pre–clinical development of farnesyltransferase inhibitors," *Cancer and Metastasis Reviews*, 17:203–210 (1998).

H. Mo, et al., "IC$_{50}$ Values for the Suppression of B16 Melanoma Cell Proliferation by Monoterpenoid Derivatives," *Exper. Biol.*, Apr. 21, 1998, 1999 meeting (Abstract).

H. Mo and C.E. Elson, "Apoptosis and Cell–Cycle Arrest in Human and Murine Tumor Cells are Initiated by Isoprenoids," *Biochemical and Molecular Action of Nutrients*, pp. 1–10 (1999).

H. Mo, D.M. Peffley and C.E. Elson, "Targeting the Action of Isoprenoids and Related Phytochemicals to Tumors," Chap. 25, *Nutritional Oncology*, pp. 379–391 (1999), Academic Press.

P. Prasanna, et al., "Lipid Metabolism as a Target for Brain Cancer Therapy: Synergistic Activity of Lovastatin and Sodiuim Phenylacetate Against Human Glioma Cells," *J. Neurochemistry*, 66:710–716 (1996).

(List continued on next page.)

*Primary Examiner*—Christopher Tate
(74) *Attorney, Agent, or Firm*—Quarles & Brady LLP

(57) ABSTRACT

A method of inhibiting or preventing the growth of tumor cells is disclosed. In one embodiment, this method comprises the step of administering a compound selected from the group consisting of citracetal, citral dimethyl acetal, citral diethyl acetal, geranyl benzoate, geranyl tiglate, geranyl anthranilate, farnesyl benzoate, farnesyl anthranilate, farnesyl tiglate, farnesyl acetate and combinations thereof to a human tumor patient, wherein the amount is effective to reduce or inhibit tumor growth by at least 50%.

5 Claims, 9 Drawing Sheets

OTHER PUBLICATIONS

A.A. Qureshi, et al., "Dietary α–Tocopherol Attenuates the Impact of γ–Tocotrienol on Hepatic 3–Hydroxy–3–Methylglutaryl Coenzyme A Reductase Activity in Chickens," *Biochemical and Molecular Roles of Nutrients,* pp. 389–394 (1996), American Institute of Nutrition.

W.N. Setzer, et al., "An Antibacterial Vitamin E Derivative from *Tovomitopsis psychotriifolia,*" *Planta Med.,* 61:275–276 (1995).

S.M. Shoff, et al., "Concentration–dependent Increase of Murine P388 and B16 Population Doubling Time by the Acyclic Monoterpene Geraniol," *Cancer Research,* 51:37–42 (Jan. 1, 1991).

D. Westfall, et al., "Metabolism of Farnesol: Phosphorylation of Farnesol by Rat Liver Microsomal and Peroxisomal Fractions," *Biochem. Biophys. Res. Comm.,* 230:562–568 (1997), Academic Press.

S.G. Yu, et al., "Geraniol, an Inhibitor of Mevalonate Biosynthesis, Suppresses the Growth of Hepatomas and Melanomas Transplanted to Rats and Mice," *Biochemical and Molecular Roles of Nutrients,* pp. 2763–2767 (1995), American Institute of Nutrition.

Z. Aharonson, et al., "Stringent structural requirements for anti–Ras activity of S–prenyl analogues," *Biochem. Biophys. Acta* 1406(1):40–50, 1998 (Abstract).

L.H. Cohen, et al., "Different analogues of farnesyl pyrophosphate inhibit squalene synthase and protein: Farnesyltransferase to different extents," *Biochem. Pharmac.* 49(6):839–845, 1995 (Abstract).

L.H. Cohen, et al., "Inhibition of human smooth muscle cell proliferation in culture by farnesyl pyrophosphate analogues, inhibitors of in vitro protein: Farnesyl transferase," *Biochem. Pharmac.* 57(4):365–373, 1999.

I. Gaon, et al., "Farnesyl and geranylgeranyl pyrophosphate analogs incorporating benzoylbenzyl ethers: Synthesis and inhibition of yeast protein farnesyltransferase," *Tetrahedron Let.* 37 (49):8833–8836, 1996 (Abstract).

R.J. Hohl, et al., "Stereochemistry–dependent inhibition of RAS farnesylation by farnesyl phosphonic acids," *Lipids* 33(1):39–46, 1998 (Abstract).

M.S. Kang, et al., "Farnesyl–derived inhibitors of ras farnesyl transferase," *Biochem. Biophys. Res. Commun.* 217(1):245–249, 1995 (Abstract).

D. Marciano, et al., "Farnesyl derivatives of rigid carboxylic acids–inhibitors of ras–dependent cell growth," *J. Med. Chem.* 38(8):1267–1272, 1995 (Abstract).

M. Marom, et al., "Selective inhibition of Ras–dependent cell growth by farnesylthiosalicylic acid," *J. Biol. Chem.* 270(38):22263–22270, 1995 (Abstract).

T.E. Meigs, et al., "Farnesyl acetate, a derivative of an isoprenoid of the mevalonate pathway, inhibits DNA replication in hamster and human cells," *Exper. Cell Res.* 219(2):461–470, 1995 (Abstract).

T. Nagase, et al., "Inhibition of cell growth of human hepatoma cell line (Hep G2) by a farnesyl protein transferase inhibitor: A preferential suppression of ras farnesylation," *Internat. J. Canc.* 65(5):620–626, 1996 (Abstract).

T. Nagase, et al., "Manumycin and gliotoxin derivative KT7595 block Ras farnesylation and cell growth but do not disturb lamin farnesylation and localization in human tumour cells," *Brit. J. Canc.* 76(8):1001–1010, 1997 (Abstract).

W. Wang and R.J.B. Macaulay, "Apoptosis of medulloblastoma cells in vitro follows inhibition of farnesylation using manumycin A," *Internat. J. Canc.* 82(3):430–434, 1999 (Abstract).

Y. Xu, et al., "Inhibition of capacitative Ca–2+ entry into cells by farnesylcysteine analogs," *Molec. Pharma.* 50(6):1495–1501, 1996 (Abstract).

W. Yang, et al., "Advances in the development of farnesyltransferase inhibitors: Substrate recognition by protein farnesyltransferase," *J. Cell. Biochem. Suppl.* 0(27):12–19, 1997 (Abstract).

| COMPOUND | STRUCTURE | POTENCY RELATIVE TO PERILLYL ALCOHOL | IC50 (µMOL/L) | SOURCE |
|---|---|---|---|---|
| MYRCENE | 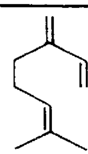 | 0.2 | >1000 | AF&F |
| FARNESENE | 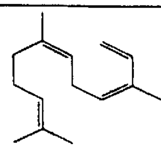 | 0.3 | 750 | BDP&FI |
| CITRONELLIC ACID | 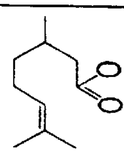 | 0.4 | 650 | AF&F |
| NERYL ACETATE | 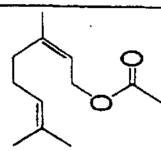 | 0.5 | 555 | BDP&FI |
| CITRONELLOL | 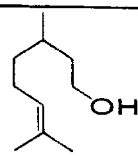 | 0.6 | 415 | BDP&FI |
| CITRONELLYL PROPRIONATE | 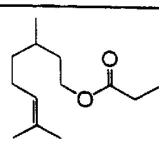 | 0.6 | 400 | AF&F |
| CITRONELLAL | 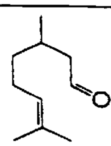 | 0.7 | 350 | AF&F |
| NEROL | 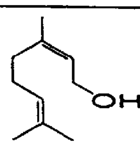 | 0.8 | 332 ± 33 | AHFC |

FIG. 1A

| COMPOUND | STRUCTURE | POTENCY RELATIVE TO PERILLYL ALCOHOL | IC50 (µMOL/L) | SOURCE |
|---|---|---|---|---|
| NERYL ACETONE | 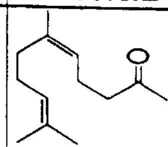 | 0.8 | 308 ± 25 | AF&F |
| PERILLYL ALCOHOL | 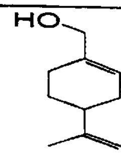 | 1.0 | 250 ± 28 | AF&F |
| GERANYL ISOBUTYLATE | 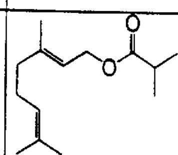 | 1.3 | 200 | BDP&FI |
| GERANYL FORMATE | 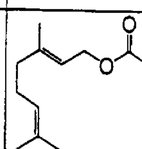 | 1.4 | 180 | BDP&FI |
| GERANYL ACETONE | 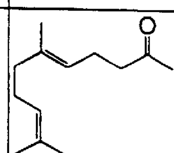 | 1.5 | 170 ± 35 | BDP&FI |
| GERANYL ACETATE | 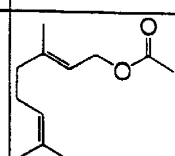 | 1.6 | 160 | SCC |
| GERANYL BUTYLATE | 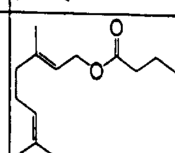 | 1.7 | 150 | BDP&FI |
| GERANYL CAPRYLATE | 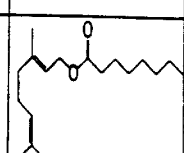 | 1.7 | 150 | BDP&FI |

| COMPOUND | STRUCTURE | POTENCY RELATIVE TO PERILLYL ALCOHOL | IC50 (µMOL/L) | SOURCE |
|---|---|---|---|---|
| GERANIOL | 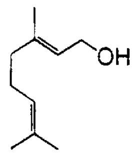 | 1.7 | 145 ± 20 | AHFC |
| GERANYL ISOVALERATE | 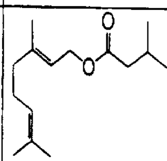 | 2.8 | 88 ± 4 | BDP&FI |
| CITRAL DIETHYL ACETAL | 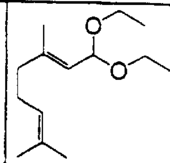 | 3.2 | 77 ± 29 | BDP&FI |
| GERANYL PHENYLACETATE | 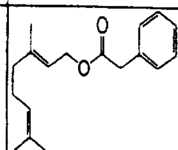 | 3.4 | 73 ± 9 | AF&F |
| CITRAL DIMETHYL ACETAL | 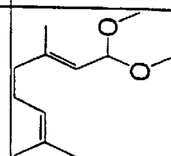 | 3.8 | 65 ± 14 | BDP&FI |
| FARNESYL BENZOATE | 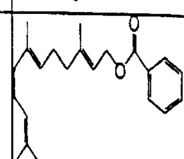 | 4.3 | 58 ± 6 | BDP&FI |
| FARNESYL TIGLATE | 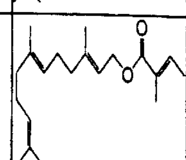 | 4.5 | 56 ± 16 | BDP&FI |
| CITRACETAL | 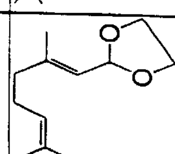 | 4.6 | 54 ± 16 | BDP&FI |

FIG. 1C

| COMPOUND | STRUCTURE | POTENCY RELATIVE TO PERILLYL ALCOHOL | IC50 (µMOL/L) | SOURCE |
|---|---|---|---|---|
| FARNESOL (TRANS, TRANS) | 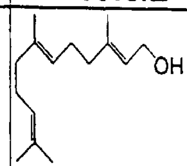 | 4.9 | 51 ± 4 | BDP&FI |
| FARNESYL ACETATE | 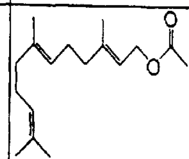 | 5.0 | 50 | AHFC |
| GERANYL BENZOATE | 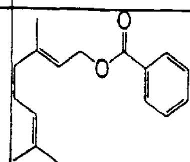 | 5.3 | 47 ± 10 | BDP&FI |
| FARNESYL ANTHRANILATE | 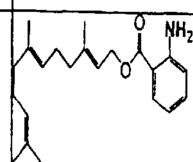 | 5.6 | 45 ± 6 | BDP&FI |
| GERANYL TIGLATE | 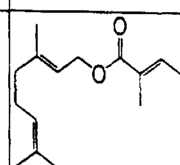 | 6.6 | 38 ± 5 | AF&F |
| GERANYL ANTHRANILATE | 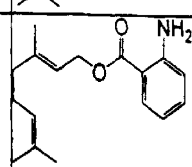 | 8.3 | 30 ± 4 | BDP&FI |
| CITRAL (NERAL + GERANIAL) | 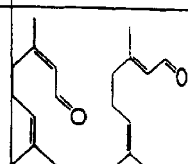 | 8.6 | 29 ± 7 | AHFC |

*AF&F: ALDRICH FLAVORS & FRAGRANCES
AHFC: ALDRICH FINE CHEMICALS
BDP&FI: BEDOUKIAN DISTINCTIVE PERFUME & FLAVOR INGREDIENTS
SCC: SIGMA CHEMICAL COMPANY

FIG. 1D

ACYCLIC MONOTERPENOID DERIVATIVES

CROSS-REFERENCE TO RELATED APPLICATION

This application claims priority to U.S. Ser. No. 60/077,734 filed Mar. 12, 1998, incorporated by reference herein.

STATEMENT REGARDING FEDERALLY SPONSORED RESEARCH OR DEVELOPMENT

This invention was made with the United States government support awarded by the following agencies: NIH Grant No: CA73418 and USDA Hatch No: 2656. The United States has certain rights in this invention.

BACKGROUND OF THE INVENTION

Cell proliferation requires the transfer of mevalonate pathway intermediates to a group of proteins, small G-proteins and the nuclear lamins among others. Agents targeted to the inhibition of the transfer process (farnesylation, geranylgeranylation), e.g., farnesyl mimetics and perillyl alcohol, have potential value as chemotherapeutic agents. Agents that block the synthesis of the mevalonate pathway intermediates, e.g., inhibitors of 3-hydroxy-3-methylglutaryl coenzyme A (HMG CoA) reductase (statins) and mevalonate kinase (sodium phenylacetate) also have therapeutic potential. The statins competitively inhibit HMG CoA reductase activity. Diverse end products of plant mevalonate metabolism (pure and mixed isoprenoids) suppress HMG CoA reductase activity (Elson, 1995; Elson and Qureshi, 1995; Elson and Yu, 1994).

The endogenous isoprenoids, the monoterpene and sesquiterpene alcohols geraniol and farnesol, also suppress reductase activity. Geraniol attenuates the HMG CoA reductase mRNA translational efficiency and decreases reductase mRNA (Elson, et al., 1998). Farnesol attenuates reductase mRNA translational efficiency and signals the proteolytic degradation of HMG CoA reductase (Correll, et al., 1994). These isoprenoids accumulate in mammalian cells only in the presence of excess mevalonate. These prenyl alcohols have relatively short biological half-lifes as they are rapidly converted to $\alpha,\omega$-prenyl dicarboxylic acids by cytosolic dehydrogenase and microsomal monooxygenase activities which sequentially catalyze the formation of prenyl aldehydes, $\alpha$-prenoic acids, $\omega$- and $\omega$-3-hydroxy-$\alpha$-prenoic acids and $\alpha,\omega$-prenyl dicarboxylic acids (Christophe and Popják, 1961; Gonzales-Pacanowska, et al., 1988; Austin, et al., 1988; Keung, 1991; Giron, et al., 1993).

Pentobarbital, an inducer of the microsomal P450 monooxygenase activity that catalyzes the formation of $\omega$- and $\omega$-3 hydroxy-$\alpha$-prenoic acids, totally reverses the isoprenoid-mediated suppression of HMG CoA reductase activity (Yu, et al., 1994). These inducible activities decrease the half-life of the endogenous isoprenoids (geraniol and farnesol) that down-regulate reductase activity.

Degradation of Endogenous Isoprenoids

Prenyl diphosphates (Geranyl-PP, Farnesyl-PP)
↓ Microsomal diphosphatase
Prenyl alcohols (Geraniol, Farnesol)
↓ Cytosolic Prenyl Alcohol Dehydrogenase
Prenyl aldehydes (Geranial, Farnesal)
↓ Cytosolic Prenyl Aldehyde Dehydrogenase
$\alpha$-Prenoic acids (Geranoic acid, Farnesoic acid)
↓ Monooxygenase, cytochrome P450 IIB
↓ $\omega,\omega$-3-hydroxylation, oxidation
$\alpha,\omega$-Prenyl dicarboxylic acids (Hildebrandts Acids)

Geraniol (Shoff, et al., 1991; He, et al., 1997; Burke, et al., 1997) and farnesol (Miquel, et al., 1996; He, e t al., 1997; Burke, et al., 1997) suppress the proliferation of cells, an action reversed by supplements of mevalonate pathway metabolites (Shoff, et al., 1991). Perillyl alcohol (a cyclic monoterpene) attenuates the HMG CoA reductase mRNA translational efficiency (Elson, et al., 1998) and suppresses cell proliferation (He, et al., 1997). Farnesyl amine (Kothapalli, et al., 1993) and perillyl amine (Burke et al., 1997) suppress cell proliferation with greater potency than the corresponding alcohol, perhaps because of their less efficient degradation.

BRIEF SUMMARY OF THE INVENTION

The present invention is a method of inhibiting the growth of tumor cells. In one embodiment, this method comprises the step of administering an effective amount of a compound selected from the group consisting of citracetal, citral dimethyl acetal, citral diethyl acetal, geranyl benzoate, geranyl tiglate, geranyl anthranilate and combinations thereof to a tumor patient. The amount is effective to inhibit or prevent tumor cell proliferation or growth. Preferably, the inhibition is at least 50% of control growth. More preferably, the inhibition is 80%. Most preferably, the inhibition is 100%.

In another embodiment of the present invention, a 15-carbon sesquiterpenoid structure has replaced the 10-carbon monoterpenoid structure in the compounds described above. Therefore, farnesyl derivatives, such as farnesyl tiglate and farnesyl anthranilate, are very active compounds and suitable for the present invention.

In another embodiment, the present invention is a pharmaceutical composition effective to inhibit or prevent the growth of tumor cells comprising a compound selected from the group consisting of citracetal, citral dimethyl acetal, citral diethyl acetal, geranyl benzoate, geranyl tiglate, geranyl anthranilate and combinations thereof and a pharmaceutically acceptable carrier. In a preferred embodiment of the present invention, the compound is selected from the group consisting of geranyl tiglate, geranyl anthranilate and combinations thereof.

In another embodiment, the present invention is a pharmaceutical composition, as described above, but substituting the 15-C compound, preferably farnesyl anthranilate, farnesyl benzoate, farnesyl tiglate or farnesyl acetate.

In a most preferred embodiment, the pharmaceutical preparation allows for the total dose of compound of 1–2 g per day per 150 lb. human. In a preferred embodiment, the dose is between 1 and 4 g per day per 150 lb. human.

It is an object of the present invention to provide an effective chemotherapeutic. Preferably, this chemotherapeutic has a relative potency to that of perillyl alcohol of at least 5 times, preferably 6 times. Potency is indicated by the $IC_{50}$ value, the concentration of a compound required to express cell growth by 50%. A lower $IC_{50}$ indicates higher potency. Therefore, a higher ratio indicates higher potency.

It is an advantage of the present invention to provide a chemotherapeutic of similar attributes to perillyl alcohol but effective at approximately 20% of the dosage of perillyl alcohol necessary to inhibit or prevent tumor cell growth.

DESCRIPTION OF THE SEVERAL VIEWS OF THE DRAWINGS

FIGS. 1A–D illustrate the structures of geraniol and farnesyl derivatives, $IC_{50}$ values, and potencies relative to that of perillyl alcohol. FIG. 1A illustrates myrcene, farnesene, citronellic acid, neryl acetate, citronellol, citronellyl proprionate, citronellal and nerol. FIG. 1B illustrates neryl acetone, perillyl alcohol, geranyl isobutylate, geranyl formate, geranyl acetone, geranyl acetate, geranyl butylate and geranyl caprylate. FIG. 1C illustrates geranial, geranyl isovalerate, citral diethyl acetal; geranyl phenylacetate, citral dimethyl acetal, farnesyl benzoate, farnesyl tiglate and citracetal. FIG. 1D illustrates farnesol (trans, trans), farnesyl acetate, geranyl benzoate, farnesyl anthranilate, geranyl tiglate, geranyl anthranilate and citral (neral+geranial).

DETAILED DESCRIPTION OF THE INVENTION

A. In General

Figure 1B:
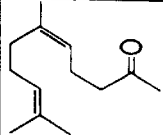
Figure 1B:
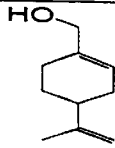
Figure 1B:
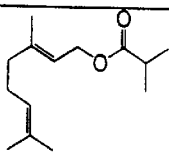
Figure 1B:
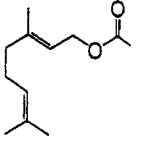
Figure 1B:
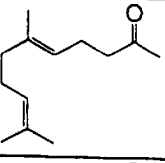
Figure 1B:
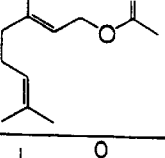
Figure 1B:
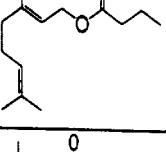
Figure 1B:
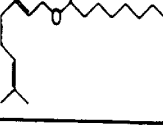

The present invention is a method of inhibiting or preventing tumor cell growth comprising the step of exposing tumor cells to an amount of a compound selected from the group consisting of citracetal, citral dimethyl acetal, citral diethyl acetal, geranyl benzoate, geranyl tiglate and geranyl anthranilate and combinations thereof effective to inhibit or prevent tumor cell growth. Preferably, the compound is either geranyl tiglate or geranyl anthranilate or combinations thereof.

In another embodiment of the present invention, a 15-carbon sesquiterpenoid structure has replaced the 10-carbon monoterpenoid structure in the compounds described above. Therefore, farnesyl anthranilate, farnesyl benzoate and farnesyl tiglate and combinations thereof are also suitable. We envision that one may wish to combined the 10-carbon and 15-carbon compounds.

Most preferably, the compound is orally administered to a tumor patient. We envision that the compound will most preferably be encapsulated or combined with a food product. Alternatively, the composition could be in tablet or liquid format. In a second preferred embodiment, the compound is administered as a salve.

The administered preparation typically comprises a pharmaceutically acceptable carrier and a composition selected from the group consisting of citracetal, citral dimethyl acetal, citral diethyl acetal, geranyl benzoate, geranyl tiglate, geranyl anthranilate and combinations thereof. The amount of the preparation is effective to diminish or inhibit tumor cell growth by at least 50% and preferably 80%. Most preferably, tumor cell growth is inhibited 100%.

Preferable doses for the compounds of the present invention are 1–4 9 per day per 150 lb. human patient. Most preferably, the dose is 1–2 g per day per 150 lb. human patient.

All of the geranyl derivative and farnesol compounds of the present invention are GRAS or FEMA and have toxicities indicating that a chemotherapeutic amount would be well-tolerated. For example, geranyl tiglate has an oral $LD_{50}$ of 5 g/kg as measured in rat.

B. Comparative $IC_{50}$ Values $IC_{50}$ values[1] ($\mu$mol/L) for the suppression of the proliferation of melanoma B16 cells by limonene (450), perillyl alcohol (250), geraniol (150) and farnesol (50) show that the acyclic monoterpene, geraniol, and the acyclic sesquiterpene, farnesol, have greater potency than the monocyclic monoterpenes. However, geraniol and farnesol undergo further oxidation prior to excretion via the kidney. We have surveyed the tumor-suppressive activity of a number of geraniol derivatives that may have a longer in vivo half-life. We report findings that citracetal, citral dimethyl acetal, citral diethyl acetal, geranyl benzoate, geranyl tiglate and geranyl anthranilate have in vitro tumor suppressive activities 5-fold greater than perillyl alcohol. These derivatives may have the advantage in being effective at lower doses than perillyl alcohol and in having a longer half-life than geraniol, geranial and farnesol.

[1]Concentration of an isoprenoid that suppresses the 40 hour cell count by 50%.

The agents suppress the in vitro growth of the highly metastatic murine B16 melanoma. This tumor cell line is more resistant than human tumor cell lines to isoprenoid-mediated growth suppression. Where tested, results of in vitro tests parallel in vivo responses. These agents are approved for food and/or cosmetic use:

|  | FEMA | TSCA |
| --- | --- | --- |
| citracetal |  | X |
| citral dimethyl acetal | 2305 | X |
| citral diethyl acetal | 2304 | X |
| geranyl benzoate | 2511 | X |
| geranyl tiglate |  | X |
| geranyl anthranilate |  | X |

TSCA: Registered under Toxic Substances Control Act for use in cosmetics, foods and food additives.

C. EXAMPLES

1. Background

Our finding that HMG CoA reductase activity is suppressed by the tocotrienols but not by the tocopherols (Qureshi, et al., 1986) led us to evaluate the reductase-suppressive potency of geraniol (Fitch, et al., 1989). Geraniol might be viewed as a structural analogue of the side chain of the tocotrienols. We subsequently reported that lemongrass oil (a GRAS substance consisting essentially of geraniol and citral) administered to 22 hypercholesterolemic subjects (140 mg/day) effected a lowering of serum cholesterol that approached significance (P<0.06). On further analysis we found that one subset of the subjects (n=14) did not respond to the treatment whereas the second (n=8) experienced an 11% (P<0.025) decrease in serum cholesterol. Cholesterol values for these responding subjects returned to prestudy levels following the termination of the study (Elson, et al., 1989).

Following up on the emerging evidence that an intermediate diverted from the mevalonate (cholesterogenic) pathway play an essential role in cell division (reviewed in Shoff, et al., 1991) we tested the impact of geraniol and mevinolin, a competitive reductase inhibitor, on the proliferation of murine P388 leukemic and B16 melanoma cells. On finding similar in vitro responses Shoff, et al. (1991) fed a diet containing 0.1% geraniol (10 g; 65 mmol/kg diet) for 14 days prior to and following the i.p. implantation of P388 leukemia cells. The median survival time was increased by 50% (24 to 36 days) and 20% of the mice remained tumor free through 50 days.

Yu, et al. (1995) fed geraniol (3.5 g; 23 mmol/kg diet) to buffalo rats for 14 days prior to and following the implantation of Morris 7777 hepatomas. At 27 days the mean volume of hepatomas in the experimental rats was 16% (P<0.001) that of the controls. Yu, et al. then fed geraniol (1 g; 6.5 mmol/kg diet and 10 g; 65 mmol/kg diet) to mice for 14 days prior to and following the implantation of melanoma B16 tumor cells. At 21 days post transplant the weight of tumors excised from mice receiving the geraniols were 70% P<0.02) and 56% (P<0.02) that of the control. In these studies, geraniol had no negative effect on weight gain.

Burke, et al. (1997) compared the impacts of perillyl alcohol (40 g; 263 mmol/kg diet), geraniol (20 g; 130 mmol/kg diet) and farnesol (20 g; 90 mmol/kg diet) on the growth of implanted pancreatric tumors. Hamsters were acclimated to the diets for one week prior to tumor implant. At 25 days post-implant the average diameter of tumors in groups of hamsters receiving perillyl alcohol, geraniol, and farnesol were 55% (NS), 15% (P<0.025), and 23% (P<0.05) respectively that of the control group. Burke, et al. then fed the geraniol and farnesol diets to hamsters following the detection of a pancreatric tumor. At 20 days, the average diameter of tumors in hamsters receiving the experimental diets was 25% (P<0.05) that recorded for the controls. In these studies, the geraniol had no negative effects on weight change.

2. Selection of Compounds

Our search of chemical (Aldrich) and Flavors and Fragrances (Bedoukian Research, Aldrich) catalogs for structural analogs of geraniol that might be resistant to degradation led us to test a number of derivatives of geraniol (and citral). Several had little impact on the proliferation of melanoma cells (Table 1).

TABLE 1

Derivatives with low potency.

| | $IC_{50}$ ($\mu$mol/L) | Growth, % of control |
|---|---|---|
| Linalool | 300 | 65 |
| Citronellal | 300 | 80 |
| Citronellyl tiglate | 150 | 32 |
| Geraniol | 150 | 50 |
| Geranyl acetone | 300 | 40 |
| Geranyl acetate | 300 | 33 |
| Geranyl butyrate | 100 | 50 |
| Geranyl caprylate | 100 | 84 |
| Geranyl formate | 100 | 52 |
| Geranyl isabutyrate | 100 | 50 |
| Geranyl isovalerate | 100 | 89 |
| Geranyl proprionate | 100 | 100 |
| Perillyl alcohol | 250 | 50 |

Figure 3:
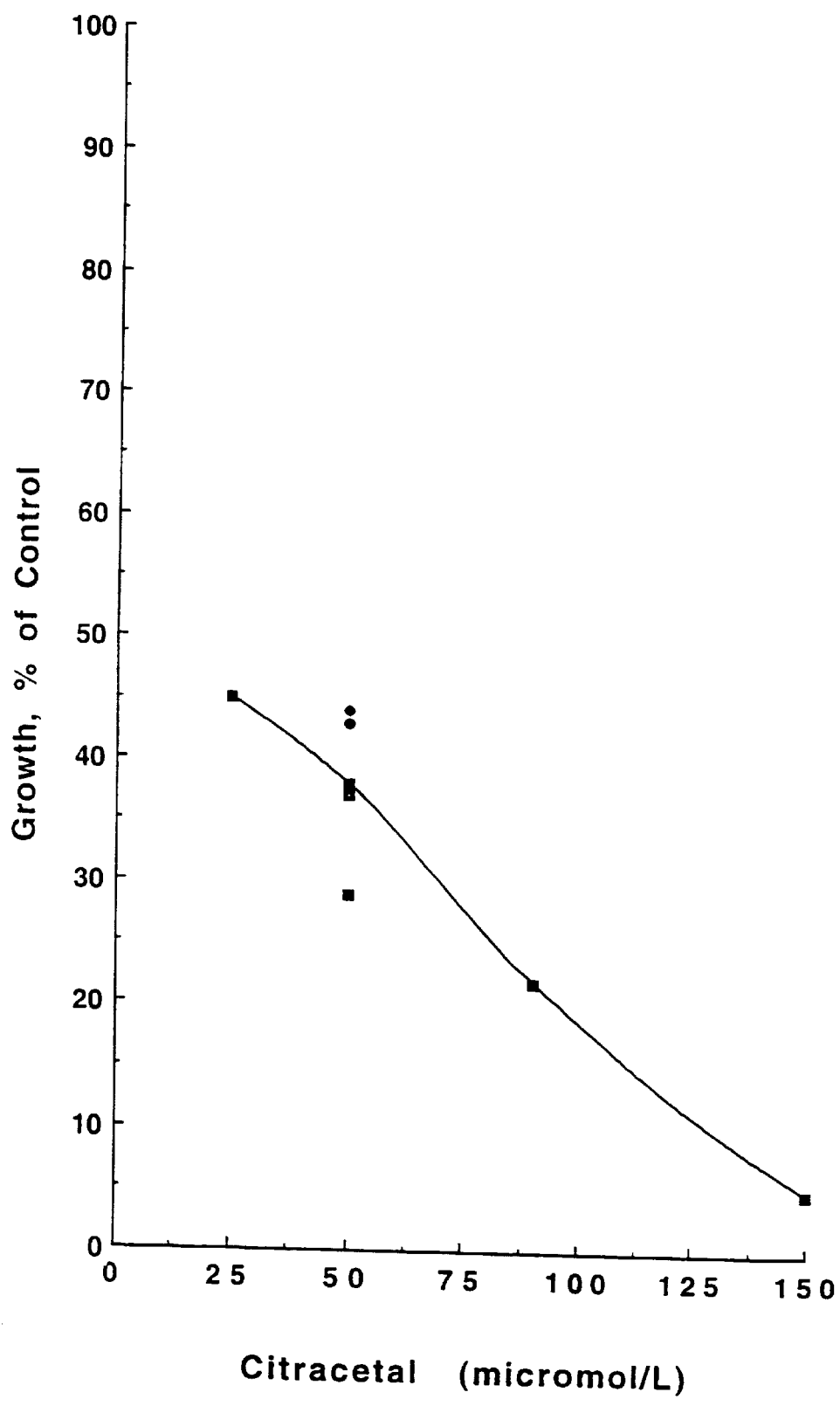
Figure 4:
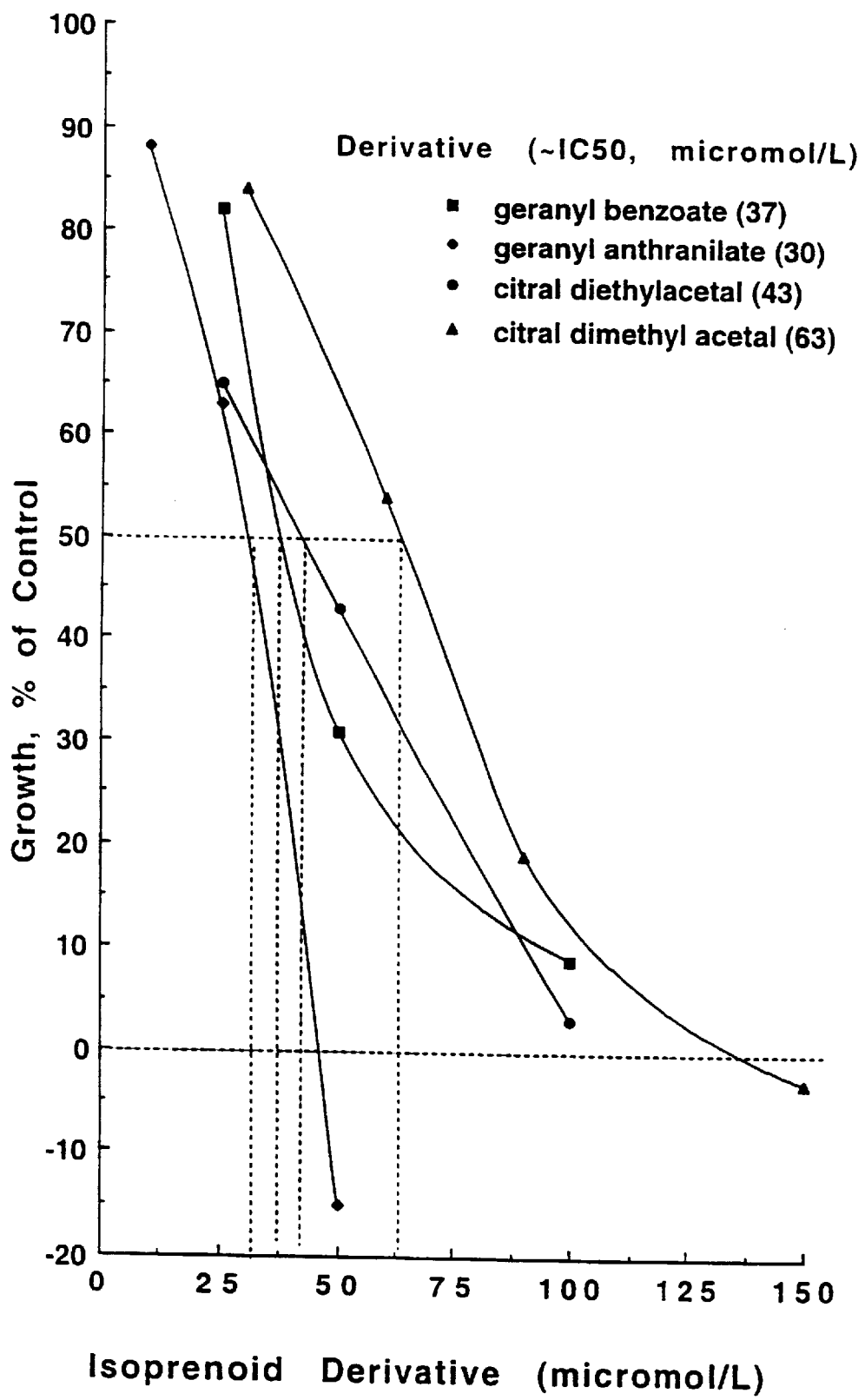
Figure 5:
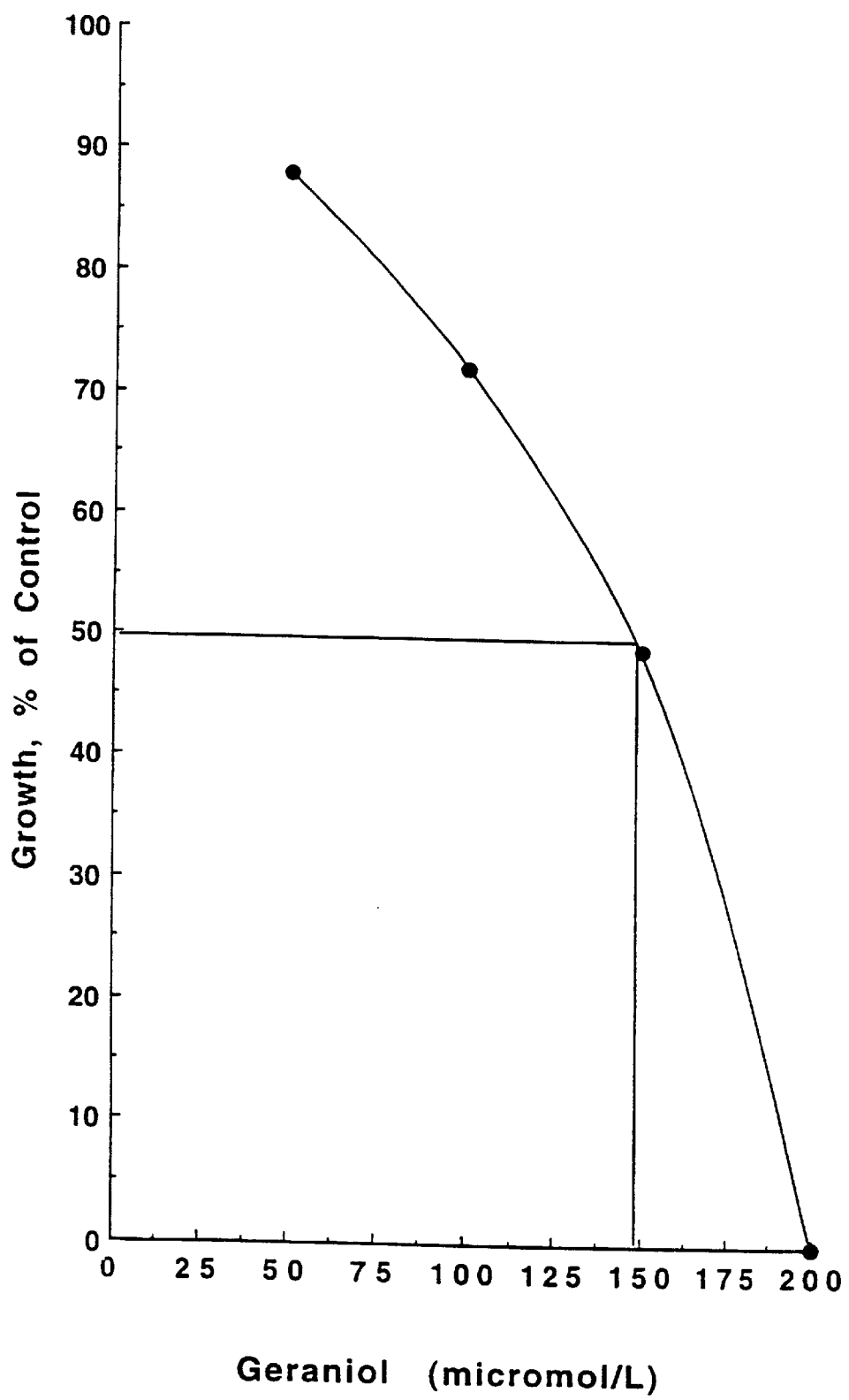
Figure 6:
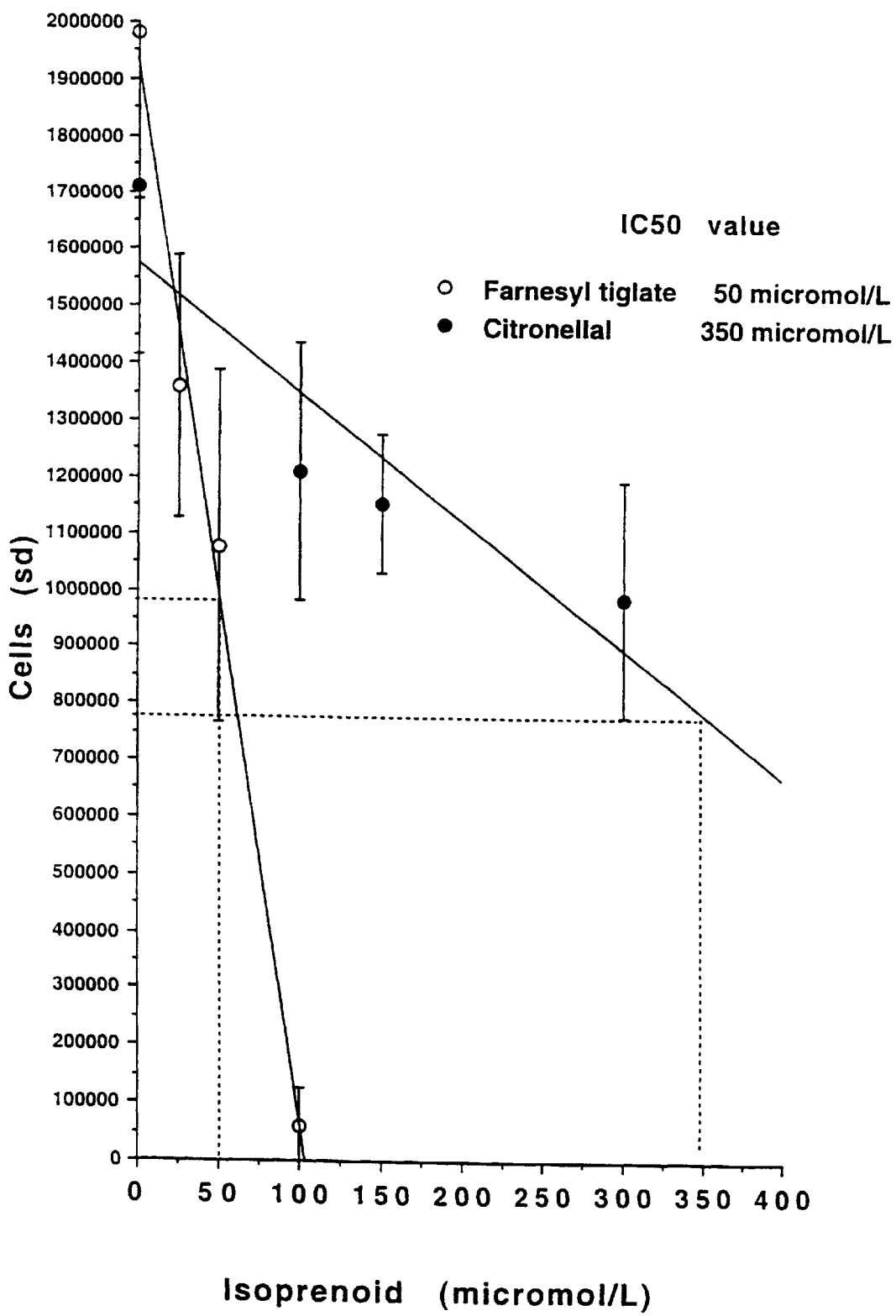

However, we identified six 10-carbon derivatives which have potency according to our screening assay several fold greater (FIGS. 2–4) than geraniol (FIG. 5, Table 1) and equal to t hat of farnesol. We have also identified active compounds in which a 15-carbon sesquiterpenoid structure replaces the 10-carbon monoterpenoid structure (FIG. 6, Table 1).

3. Materials and Methods $IC_{50}$ Determinations: Murine B16(F10) melanoma cells, a tumor cell line with high metastatic potential (Tsukamoto, et al., 1991) were grown in monolayer culture (35×10 mm flasks) in 3 mL RMPI 1640 media (Sigma) supplemented with 10% newborn calf serum (GIBCOBRL, Grand Island, N.Y.) and 80 mg/L gentamycin (Sigma, St. Louis, Mo.). Cultures, seeded with 1–1.5×10$^5$ cells, were incubated for 24 hours at 37° C. in a humidified atmosphere of 5% $CO_2$. Isoprenoids, dissolved in absolute ethanol, were added at 24 hours (0 time); all cultures contained 5 mL ethanol/L (85 mmol/L). The cultures were incubated for an additional 48 hours. The medium was removed and the monolayers were washed twice with Hanks' Balanced Salt Solution (Sigma) and then incubated with a trypsin-EDTA solution (Sigma) at 37° C. for 2 minutes. Trypsin was inactivated by suspending the cells in medium containing 10% fetal bovine serum (Sigma). The cells were pelleted at 250×g and resuspended in Hanks' Balanced Salt Solution. Viable cells, cells that excluded 0.4% trypan blue (GIBCOBRL), were counted with a hemocytometer; 24 hour cell counts were deducted from final cell counts to provide an estimate of the net increase in cell number. The concentration of an isoprenoid required to inhibit the net increase in the 48 hour cell count by 50% ($IC_{50}$) is determined from plots of data. (Mo, et al., 1998).

FIG. 1 discloses structures of diverse isoprenoids, selected derivatives, the $IC_{50}$ value and potency of each isoprenoid relative to that of perillyl alcohol (250 $\mu$mol/L) and source. The $IC_{50}$ value is the concentration of the isoprenoid required to suppress the net increase in the population of B16 melanoma cells by 50%. FIGS. 2–6 are plots of murine B16 (F10) melanoma cell growth response to geranyl tiglate (FIG. 2), citracetal (FIG. 3), geranyl anthranilate, geranyl benzoate, citral diethylacetal, and citral dimethylacetal (FIG. 4), geraniol (FIG. 5) and farnesyl tiglate (FIG. 6).

Figure 2:
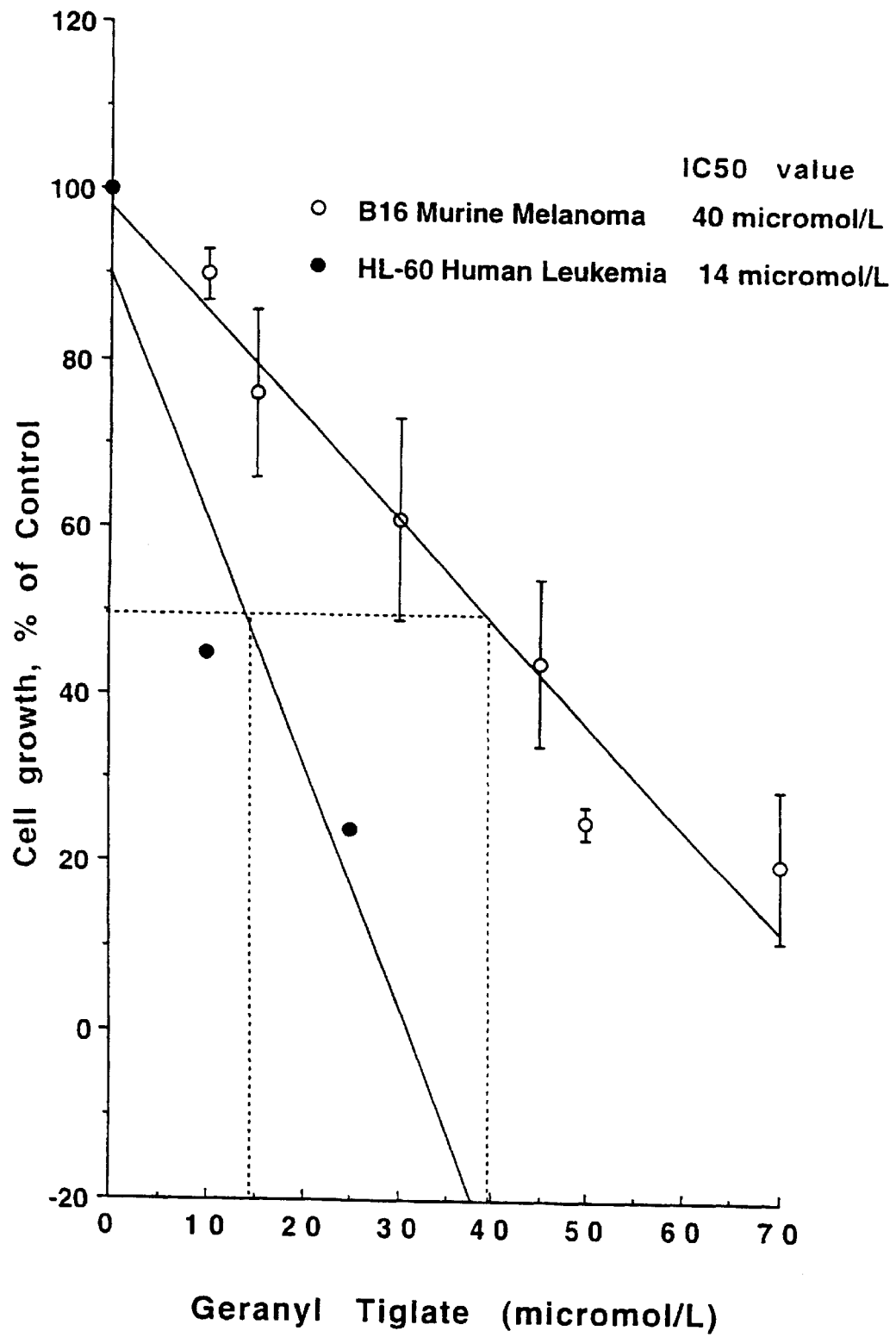
FIGS. 2–6 are plots of murine B16 (F10) melanoma cell growth response to geranyl tiglate (FIG. 2), citracetal (FIG. 3), geranyl anthranilate, geranyl benzoate, citral diethylacetal, and citral dimethylacetal (FIG. 4), geraniol (FIG. 5) and farnesyl tiglate (FIG. 6).

FIG. 2 is a plot showing the geranyl tiglate-mediated suppression of the growth of murine B16 melanoma cells and human HL-60 leukemic cells. FIG. 6 is a plot of the farnesyl tiglate-mediated and citronellal-mediated suppression of the 48 hour growth (net increase in cell number) of murine melanoma B16 cells and estimates of $IC_{50}$ values.

Human cell experiments were performed the same as the murine B16 cells, except that cell growth was monitored in suspension culture.

Human HL-60 acute promyelocytic leukemia cells (CCL-240, ATCC) were grown in suspension culture (25 cm$^2$ flasks) in 8 mL RPMI 1640 medium with 20% FBS and 2% penicillin/streptomycin. Cultures, seeded with 1.25×10$^8$ cells/L, were incubated with test agents for 24 hours at 37° C. in a humidified atmosphere of 5% $CO_2$. HL-60 cells were pelleted at 250×g and resuspended in HBSS. Viable cells, cells that excluded 0.4% trypan blue, were counted with a hemocytometer; 0-time (seeding) cell counts were deducted from final cell counts to provide an estimate of the net increase in cell number.

Isoprenoids: Citracetal, citral diethyl acetal, citral dimethyl acetal, geranyl anthranilate, geranyl benzoate, geranyl tiglate were gifts of Bedoukian Research, Inc., Danbury, Conn. and are described in greater detail below. Citral (geranial), farnesol, geraniol, d-limonene, perillyl alcohol, and perillaldehyde were purchased from Aldrich Chemical, Milwaukee, Wis. $IC_{50}$ values determined during these assays for geraniol (~150 $\mu$mol/L) and perillyl alcohol (~250 $\mu$mol/L) fall within 10% of reported values (He, et al., 1997).

Acyclic Monoterpenoid Alcohols

Geraniol: 3,7-dimethyl-2,6-octadien-1-ol
  CAS Name: 2,6-octadien-1-ol, 3,7-dimethyl-, (E)-CAS No: 106-24-1
  FEMA: 2507
  Very high quality, rose odor used in perfume and fruit flavors
  Molecular Wgt: 154.26
  Molecular Formula: $C_{10}H_{18}O$ Nerol: 3,7-dimethyl-2,6-octadien-1-ol CAS Name: 2,6-octadien-1-ol, 3,7-dimethyl-, Z)-
CAS No.: 106-25-2
FEMA: 2770
Citrus-lemon flavor used in various floral fragrances, berry flavors
Molecular Wgt: 154.25
Molecular Formula: $C_{10}H_{18}O$ Citronellol: 3,7-dimethyl-6-octen-1-ol
Linalool: 3,7-dimethyl-1-6-octadien-3-ol Acyclic Monoterpenoid Aldehydes Geranial: 3,7-dimethyl-2,6-octadien-1-al
Neral: 3,7-dimethyl-2,6-octadien-1-al
Citral: a mixture of the geometric isomers
Derivatives
Citracetal
  CAS Name: 1,3-dioxolane, 2-(2,6-dimethyl-1,5-heptadienyl)-
  CAS No.: 66408-78-4
  FEMA:
  Clean, lemony, floral odor.
  Molecular Wgt: 196.28
  Molecular Formula: $C_{12}H_{20}O_2$
Citral diethyl acetal
  CAS Name: 2,6-octadiene, 1,1-diethoxy-3,7-dimethyl-
  CAS No.: 7492-66-2
  FEMA: 2395
  Fine, fresh, citrusy odor used in perfumes and citrus flavors.
  Molecular Wgt: 226.36
  Molecular Formula $C_{14}H_{26}O_2$
Citral dimethyl acetal
  CAS Name: 2,6-octadiene, 1,1-dimethoxy-3,7-dimethyl-
  CAS No.: 7549-37-3
  FEMA: 2304
  Very pleasant, floral lemon note used in perfumes and citrus flavors.
  Molecular Wgt: 198.31
  Molecular Formula: $C_{12}H_{22}O_2$
Geranyl anthranilate
  CAS Name: 2,6-octadien-1-ol, 3,7-dimethyl-, 2-aminobenzoate, (E)-
  CAS No.: 67874-69-5
  FEMA:
  Heavy, honeysuckle odor used in perfumes (honeysuckle, gardenia).
  Molecular Wgt: 273.38
  Molecular Formula: $C_{17}H_{23}NO_2$
Geranyl benzoate
  CAS Name: 2,6-octadien-1-ol, 3,7-dimethyl-, benzoate, (E)-
  CAS No.: 94-48-4
  FEMA: 2511
  Long lasting, rosy, amber odor used in perfumes and fruit flavors.
  Molecular Wgt: 258.36
  Molecular Formula: $C_{17}H_{22}O_2$
Geranyl tiglate
  CAS Name: 2-butenoic acid, 2-methyl-, 3,7-dimethyl-2,6- octadienyl ester, (E,E)-
  CAS No.: 7785-33-3
  FEMA:
  Somewhat fruity, geranium-like odor used in geranium, rose and lavender fragrances.
  Molecular Wgt: 236.36
  Molecular Formula: $C_{15}H_{24}O_2$ Acyclic Sesquiterpenoid Alcohols Farnesyl anthranilate:
  2,6,10-dodecatrien-1-ol, 3,7,11 trimethyl-2-aminobenzoate (E, E)
Farnesyl benzoate:
  2,6,10-dodecatrien-1-ol, 3,7,11 trimethyl-benzoate (E, E)
Farnesyl tiglate:
  2,6,10-dodecatrien-1-ol, 3,7,11 trimethyl-octadienyl ester (E, E)
Farnesyl acetate
  2,6,10-dodecatrien-1-ol, 3,7,11 trimethyl-octadienyl ester (E, E)

What is claimed is:

1. A method of inhibiting or reducing the growth of tumor cells comprising the step of exposing a tumor cell farnesyl anthranilate, wherein the amount is effective to inhibit or reduce tumor cell growth.

2. A method of inhibiting or reducing the growth of tumor cells comprising the step of administering farnesyl anthranilate, wherein the amount of effective to reduce or inhibit tumor growth by at least 50%.

3. The method of claim 2 wherein inhibition of tumor cell growth is at least 50% of control growth.

4. The method of claim 3 wherein the inhibition is at least 80%.

5. The method of claim 4 the wherein inhibition is 100%.

* * * * *